United States Patent [19]

Christenbury et al.

[11] 4,000,975

[45] Jan. 4, 1977

[54] METHOD OF MEASURING DAMAGE TO GRAIN

[75] Inventors: Gerald Davis Christenbury, Florence, S.C.; Wesley Fisher Buchele, Ames, Iowa

[73] Assignee: Iowa State University Research Foundation, Inc., Ames, Iowa

[22] Filed: Jan. 12, 1976

[21] Appl. No.: 648,285

[52] U.S. Cl. .......................... 23/230 B; 260/508; 250/365; 356/51

[51] Int. Cl.² .................. G01N 21/52; G01N 33/10

[58] Field of Search .................. 23/230 B; 260/508

[56] References Cited

UNITED STATES PATENTS 3,773,827  11/1973  Schundehutte ..................... 260/508

OTHER PUBLICATIONS

Chemical Abstracts, 74:38589q (1971).
Chemical Abstracts, 81:101001d (1974).
Chemical Abstracts, 81:101169q (1974).
Chemical Abstracts, 81:131828w (1974).

*Primary Examiner*—Morris O. Wolk
*Assistant Examiner*—Sidney Marantz
*Attorney, Agent, or Firm*—Tilton, Fallon, Lungmus, Chestnut and Hill

[57] ABSTRACT

A method of measuring mechanical damage to a grain, such as corn, includes applying a reacting solution to a sample of corn. The solution contains a material, such as 8-anilino-1-naphthalene sulfonic acid, that reacts selectively with the damaged portion of the corn kernels, i.e., the internal protein that is exposed when the outer shell is penetrated or breached. Excess solution is washed off; and the kernels are dried for convenience of handling. The dried corn is ground to a uniform fineness and then spread over a predetermined area. What is inherently a three-dimensional or volume phenomena (damage) is converted to a two-dimensional or area measurement. The sample is exposed to ultraviolet light; and induced fluorescence is measured. The output of the measuring system is linearly related to, and thus a measure of the mechanical damage of the sample.

10 Claims, 5 Drawing Figures

METHOD OF MEASURING DAMAGE TO GRAIN

BACKGROUND AND SUMMARY

The present invention relates to a method of measuring damage to grain; and more particularly, it is directed to measuring the mechanical damage to grain kernels, such as corn, which occurs during harvesting, drying and handling. Although the disclosure deals specifically with corn, persons skilled in the art will readily appreciate that the method of the present invention may be applied to other grain kernels having internal protein, all of which are subject to mechanical damage during harvesting, drying and handling.

Standing in the fields, unhusked corn is undamaged and can last almost indefinitely when direct without diminishing its food value for man and animals. Deterioration begins with the mechanical process of harvesting, and practically every subsequent operation in the drying, transporting and handling further decreases the quality of the grain. The rate of deterioration is dependent on the initial injury sustained during such mechanical processes, particularly the harvesting operation. During harvesting, the corn kernels are subjected to damaging impact and compressive forces which result in breaches or cracks in the pericarp of the kernels. Mold will grow in the cracks or interstices of the corn kernels to such an extent that an entire shipment may be destroyed. Government guidelines have been established, for example, in the amount of Aflatoxin that may be found in grains. If the guidelines are exceeded, the shipment may be seized by the Food and Drug Administration. In all probability, the regulations regarding toxins in feed corn will become more stringent in the future.

Because practically no measurements are currently made concerning the concentration of toxins at the initial selling point, and no discounts applied for mechanical damage, there is little or no incentive for the actual producer of the crop to minimize mechanical damage. Further, there is no commercial apparatus or method available for measuring mechanical damage to corn as it is being harvested. If such a method were available, farmers could adjust their combines to minimize the mechanical damage which would result in great savings which could be passed on to consumers.

A number of indices or tests have been proposed for measuring mechanical damage, but these have been primarily of theoretical or academic interest. It is believed that much of the waste due to mechanical damage could be reduced or eliminated if, for example, grain elevators or markets could establish a purchase price based, at least in part, on discounts for the mechanical damage of the corn as it is delivered. This would add some incentive to the farmer to properly adjust his combine.

As indicated above, systems have been proposed for measuring mechanical damage to corn, but none of these systems have had any degree of universal acceptance.

Photoelectric quality control devices have been used to sort agricultural products for many years. For example, it was suggested that stained damaged seed be removed with commercially available color sorting equipment. The principal disadvantages of such commercial units is the high initial cost, low capacity, and need for specially trained operators.

Other workers have utilized a device to facilitate optical sorting of middle rice based on translucence differences. Seventy-five percent of the damaged kernels were removed based on differences of transmittance of individual kernels. One researcher reported that available color sorters were not suitable in evaluating corn damage.

Research workers have utilized fast green dye to facilitate visual inspection for mechanical damage or corn samples. A commercial sorter was developed and used to sort products tainted with Aflatoxin from consumable food products. This machine uses an ultraviolet light which activates a fluorescent material produced by *Aspergillis Flavus* and a photodetector to distinguish between contaminated material and the product that contains no toxins.

The use of fluorescent pigments has found wide acceptance and utility in many areas of research and commercial application in the agricultural field. Fluorescent materials have the property that, when stimulated by a suitable light source, they emit light of a longer wavelength than the incident light. In practice, ultraviolet light is used as the source, and the emission is in the visible spectrum.

In the present invention, corn kernels are treated with a reacting solution containing an agent that selectively reacts with the damaged portions of the kernels—specifically, the agent forms a fluorescent bond when it comes in contact with the kernel protein which is exposed when the outer shell of the kernel is breached. The agent may conveniently be applied in aqueous solution. The kernels are washed after application of the agent to remove the excess agent, and they are dried for convenience in handling. The treated corn is then ground to a fine powder. The exposed surface of the corn protein bonds to the agent so that after grinding, the products of the reaction which contain the agent are representative of the cumulative area of the interior of the corn exposed through breach. The powder is then spread into a uniform field and exposed to an ultraviolet light source, and the resulting fluorescent light is measured. Thus, the volumetric damaged surface is converted to an area measurement. The fluorometer response is a linear function of the area of fluorescing material. The measurement of the fluorometer is therefore proportional to the original three-dimensional area exposed through mechanical damage.

By grinding the corn prior to illuminating it to cause fluorescence, we have eliminated any dependence of the measurement system on the orientation of the corn kernels. Further, damage is measured as a function of the exposed surface. If the whole kernels were used for measurement, the shape and depth of the damage breach would have an effect on the measurement. For example, a deep, narrow cut may emit a relatively smaller amount of detectable fluorescence, whereas a shallow surface breach may expose less total area of endosperm, but result in a larger detected fluorescence. The present invention also obviates the problem of different readings due to the location of kernels relative to the transducer-sensing fluorescence, as will be clear from the detailed description below.

The present method is reliable and repeatable, and it does not take a long time to perform the test, usually less than about 5 minutes. The method may be practiced on all varieties of corn, and it is independent of the original moisture content of the sample. The present method is also inexpensive (because it is applied to and destroys only a small sample of the crops and the equipment and materials are relatively inexpensive). Further, it is simple and reliable enough to be performed by relatively unskilled labor.

Other features and advantages of the present invention will be apparent to persons skilled in the art from the following detailed description of a preferred embodiment accompanied by the attached drawing wherein identical reference numerals will refer to like parts in the various views.

THE DRAWING

DETAILED DESCRIPTION

Figure 1:
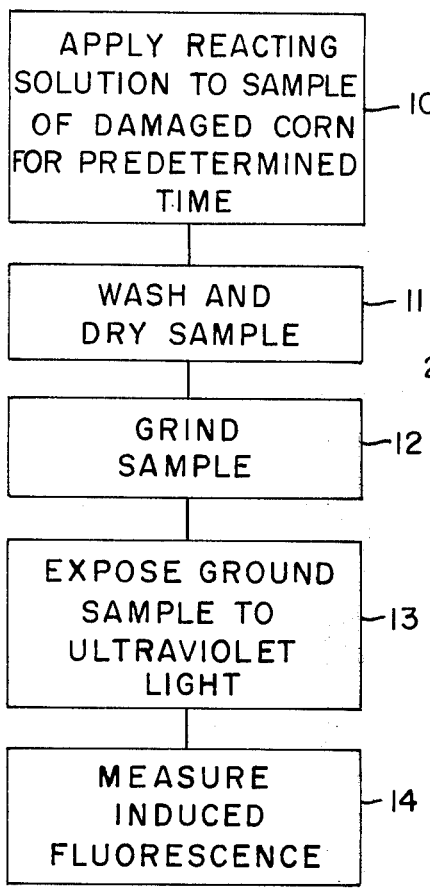
FIG. 1 is a block diagram illustrating the steps to be practiced in a preferred embodiment of the method of the present invention.

Referring first to FIG. 1, as indicated in block 10, a reacting solution is applied to a sample of the damaged corn for a predetermined time. The solution contains an agent that forms a fluorescent bond with the internal protein of the corn. Next, the sample is washed to remove excess agent, and then dried for convenience of handling, as indicated in block 11. In block 12, the sample is ground to a fine powder of generally uniform size.

Next, in block 13, the ground sample is irradiated with ultraviolet light, and as indicated in block 14, the induced fluorescence is measured. The measurement of induced fluorescence is representative of mechanical damage to the sample of corn. An important aspect of the present invention is that after the dye has been applied, the step of grinding the sample converts the ultimate measurement from a volume measurement (that is, the three-dimensional contours of the various types of breaches or mechanical damage that may be encountered) to an area measurement (as represented by the finely ground sample spread over a known surface), as will be discussed more fully below.

THE AGENT

The average composition of whole-kernel corn has been determined; and for moisture-free samples, the endosperm is approximately 9.4 percent protein and the germ is approximately 18.8 percent protein, whereas the barb or pericarp is approximately 3.7 percent protein. Since the protein content of the endosperm and the germ is much higher than that of the pericarp, a material that combines chemically with the protein to form a fluorescent compound is a good indicator of kernel fracture provided the endosperm is exposed upon breach of the seed coat. One material used as a label for protein was reported by Brand and Gohlke, "Fluorescence Probes for Structure, " ANNUAL REVIEW OF BIO. CHEM., Vol. 41, p. 843–868 (1972), is 1-anilinonaphthalene-8-sulfonate, referred to briefly as ANS and known as a dye.

In the present invention, a standard solution was prepared by mixing five grams of 8-anilino-1-naphthalene sulfonic acid (ANS) obtained from Sigma Chemical Co., St. Louis, Mo., with 500 ml. of distilled water. The ANS solution was then poured over 50 grams of corn kernels. The damage of which had previously been observed by visual inspection. The sample was soaked for 2 minutes, and then the reacting solution was poured off. The sample was then rinsed twice (block 11 of FIG. 1), and dried by placing the grains on absorbent paper towels.

Other ANS materials may also be used, such as 6-anilino-2naphthalene sulfonic acid.

CONTACT TIME OF REACTING SOLUTION

In order to evaluate the effect of the time during which the reacting solution contacted the sample, various samples of corn were taken from a single parent lot for evaluation of induced fluorescence as a function of contact time. Five 50-gram samples were placed in separate containers for testing. A first sample was considered as a control group, and was not brought into contact with the reacting solution. A second sample was covered with distilled water as a secondary control measure. A third sample was covered with the ANS solution and soaked for one minute. A fourth sample was covered with the ANS solution for 2 minutes. A fifth sample was covered with the ANS solution for 5 minutes. All samples were rinsed twice with tap water and then dried on paper towels.

Figure 4:
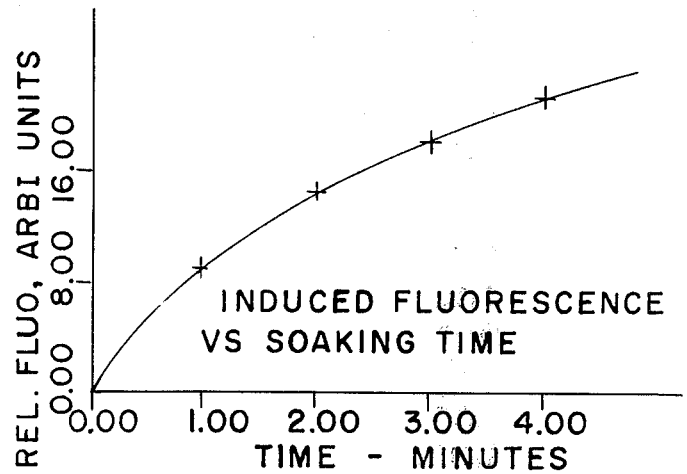
FIG. 4 is a graph showing the relationship between the relative induced fluorescent of a sample and the amount of time in which the sample was soaked in the dye solution.

After grinding to a uniform powder, the samples were separately irradiated; and the resulting induced fluorescence was measured and found to be an increasing function of contact time, as illustrated in FIG. 4. The increase is probably attributed to the fact that the ANS penetrates more deeply into the corn kernels with increasing time; and it illustrated that in comparing samples or in comparing a sample with a reference, it is important that this agent be applied to the samples for predetermined and equal times. Considering these results and the fact that it is desirable to minimize the overall time of the test, a preferred range of application times is 1–2 minutes.

GRINDING

The treated samples were ground on small laboratory Wiley mill using a No. 20 screen. A ground sample has been found to give reliable, repeatable readings of fluorescence intensity regardless of the orientation of the particular sample, due to the previously mentioned observation that what is inherently a volumetric or three-dimensional phenomena (damage) is connected to a two-dimensional field for measurement.

In other words, the importance of the grinding of the sample prior to measuring induced fluorescence is that the detection system sees an intensity of fluorescence that is a function of the original total volume of material brought into contact with the dye since the total induced fluorescence is a function of the exposed surface and penetration depth. By applying the dye solution for a predetermined time which is equal for different samples, and then grinding the samples, a relatively complicated and non-repeatable volume measurement is simply converted to a surface area measurement. Because total induced fluorescence is increased with contact time of the dye, care must be taken to limit the contact time so that the dye does not penetrate the full kernel. This is easily avoided, however.

For any given sample it can be found that the same fluorescence intensity readings will be obtained even though the sample is mixed up, provided that the sample is spread over approximately the same surface area.

MEASURING SYSTEM

Figure 2:
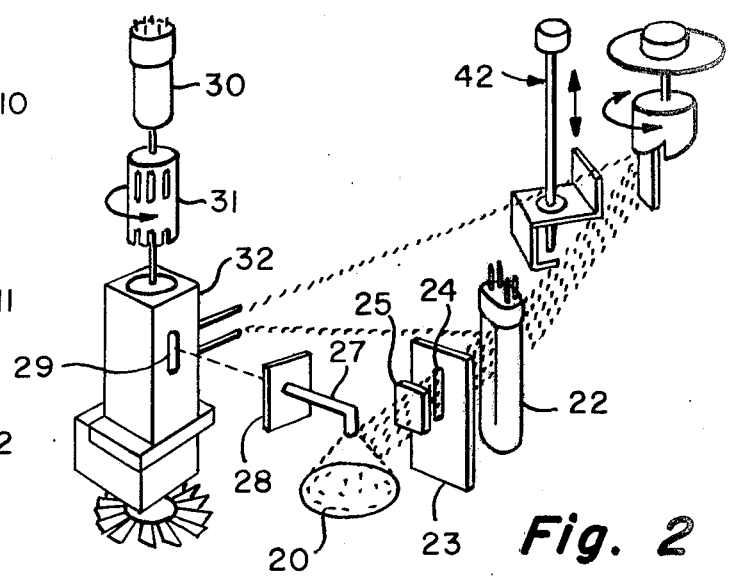
FIG. 2 is a diagrammatic view of a fluorometer which may be used in practicing the present invention.

An existing commercial fluorometer (Turner Fluorometer Model 110) was used for measuring fluorescence. Some modifications were made to the commercial machine to adapt it to the particular environment of the invention, and these will be discussed presently. Referring now to FIG. 2, reference numeral 20 indicates a holder having a generally planar bottom over which a sample of the finely ground, dyed corn is uniformly spread. The system includes a light source 22 which emits light through a range selector 23 having four separate apertures, only one of which is shown in the drawing and designated 24. Light passing through the aperture 24 is then passed through a primary or excitation filter 25.

The light source 22 is preferably a long-wave ultraviolet source. In one embodiment, a model UVS-12 ultraviolet light source was used, as manufactured by Ultraviolet Products of California, U.S.A. This light source had considerable emission in the infrared region as well as a peak near 550 nm. Thus, a filter 25 was used to limit the incident light to a known band. A Kodak 18A glass filter was used as the primary limiting filter on the light source. The light passing through the filter 25 illuminates the sample of powder uniformly spread over the holder 20.

Light emitted from the irradiated sample through fluorescence may conveniently be collected by a fiber optic transmission conduit or bundle 27.

The fiber optic bundle 27 couples the collected light through a secondary filter 28 and thence through a window 29 of a photomultiplier tube 30 which is mounted within a rotating light interrupter, both of which are mounted in a housing 32. Although in my investigation the photomultiplier of the fluorometer which was available had an S-4 spectral response, this is not the most sensitive response curve for fluorescing materials that emit in the green portion of the visible light spectrum. A response curve similar to 129 or 119 would be more sensitive, and therefore preferable. Further, for best operation there should be a separation of at least 20 to 30 nm between the frequency spectrum of the light source and the sensitivity spectrum of the photodetector. Other fluorometers may be used, and the invention, in particular, is not limited to the use of photomultiplier tubes.

In order to enhance the discrimination of the photomultiplier tube, the filter 28 was used to eliminate any scattered light and to permit transmission of only the fluoroscent light to the photomultiplier tube. A Kodak No. 53 gel filter was used as the filter 28 to filter the light transmitted to the photomultiplier tube.

The fluorometer available was designed to measure the fluorescence of solutions. This design was modified to include blanking of the internal light source, and using an external light source as disclosed above for exciting the samples. Further, a sample compartment was constructed external of the machine and it was enclosed to reduce the effect of ambient light. The fiber optic transmission conduit 27 was incorporated to transmit the fluorescent light from the sample, and the filter 28 was also added.

Figure 3:
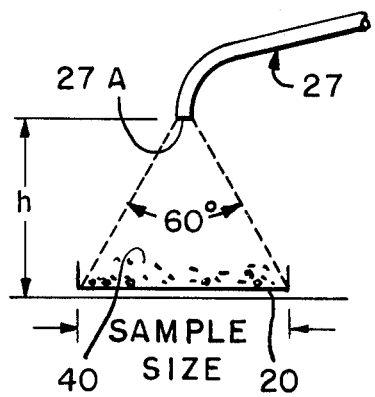
FIG. 3 is a close-up diagrammatic view showing the relationship between the optic fiber bundle used for picking up fluorescent light and the size of the samples.

The fiber optic transmission conduit 27 was obtained from Edmund Scientific Company, and it was 12 inches long and ¼ in. in diameter with a numerical aperture of 0.55 and an acceptance angle, referrng to FIG. 3, of 60°. Approximately 70 percent of the light striking the input end 27A of the fiber optic transmission conduit enters the fibers and about 8 percent of this is lost per each foot of length. The fiber optic conduit transmits wavelengths of 400 to 2,000 nm.

The fiber optic conduit was positioned above the sample holder 20 so that the 60° cone of light that would be accepted by the fiber optic conduit would encompass the hole of the sample, as seen in FIG. 3. Preferably, the size of the sample (after being finally ground) is sufficiently large to complete cover the bottom of the holder 20 as indicated by reference numeral 40 in FIG. 3.

The fluorometer indicated has a scale that goes from 1 to 100. Any range of fluorescent intensities can be adjusted to fall within this scale. The lower limit is adjusted by the blank control generally designated 42 in FIG. 2. This adjustment sets the level of residual or background fluorescence by balancing the internal optical bridge so that the output meter indicates zero. The upper limit is controlled by the intensity of the fluorescent light that reaches the photomultiplier tube 30. An increase in the intensity of the ultraviolet light incident on the damaged stained sample results in increased fluorescence. The intensity of the ultraviolet light affects the background or residual fluorescence. There must be some compensation for increased residual fluorescence when adjusting the lower limit. There are two ways of adjusting the intensity of the light that reaches the tube 30. One method of controlling the intensity is to control the spacing between the light probe 27 and the fluorescing material. The second control on the fluorescing intensity is to control the intensity of the incident ultraviolet light on the fluorescing sample. Since the quantum efficiency is constant for a particular material, the intensity of fluorescent light is a direct function of incident light energy. Because the light intensity is a square function of the incident energy on the sample, it can be controlled within relative broad limits with only small adjustments in distance between the sample and the light source.

In practice, the lower limit is determined by placing an untreated sample of corn in the sample compartment and adjusting the blank control and balance control so that the meter indicates zero. This in effect cancels out the effects of the natural fluorescence of the corn. The upper limit is found by placing the sample with the highest degree of fluorescent material in the sample compartment and adjusting the distance that the ultraviolet light source is from the treated sample so that there is an indicated reading of 100 on the fluorometer. The adjustments on the upper limit affect the lower limit. There is some trial and error in finding a suitable upper limit while maintaining the zero output for the lower limit. However, in any case, the upper limit is not a critical adjustment because we can only measure relative values of induced fluorescence which must be related to the quality factor of the grain that is of interest.

It was also found that measurements varied significantly with line voltage, so a conventional voltage regulator was used to eliminate line voltage variations.

The fluorometer, voltage regulator, and the ultraviolet light source were allowed to warm up for thirty minutes prior to taking any fluorescent readings. Once the position of the ultraviolet light and the fiber optic had been determined it was only necessary to adjust the balance control on the fluorometer to bring the instrument to zero for the untreated control prior to taking fluorescent readings on the treated samples.

The preferred method for evaluating damage by induced fluorescence includes an initial grinding of the treated samples on a small laboratory Wiley mill to a uniform particle size. Grinding the samples on the Wiley mill gave a more uniform fluorescing field than whole kernels from which to measure the induced fluorescence. The ground samples were placed in a 4 cm sample holder 20 for evaluation. The fiber optic was adjusted so that the field of view was 3.5 cm in diameter. Once the initial set-up was made, all testing with the ground samples was made without any further adjustments.

Figure 5:
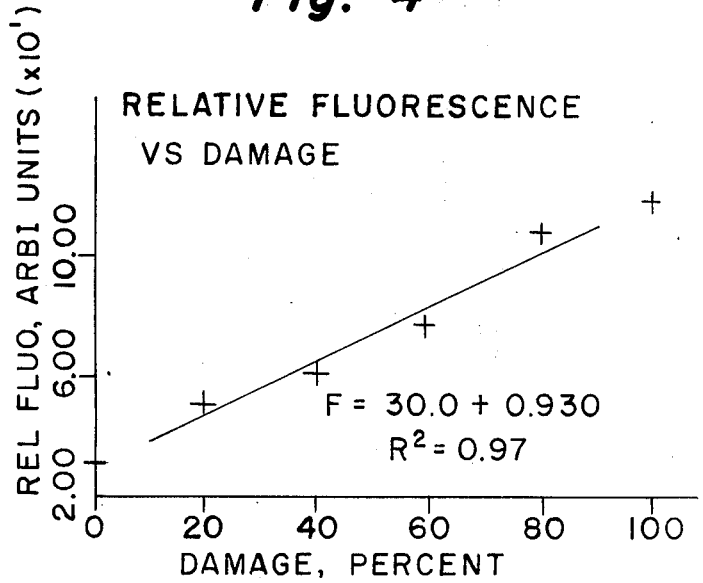
FIG. 5 is a graph showing relative fluorescence versus percent damage for samples prepared to have known amounts of damage.

To test for induced fluorescence as a measure of actual corn damage, samples of corn were prepared with a known percentage of damage for evaluation. The damaged samples were prepared by splitting corn kernels through the embryo and then mixing the split kernels with sound undamaged kernels from the same lot. The samples were mixed by weight to give 0, 20, 40, 60, 80, and 100% damage. The samples were soaked for two minutes in the aqueous ANS solution, rinsed twice, dried, and then ground on the Wiley mill using the No. 20 screen. The results of this test indicated that there is a linear increase in induced fluorescence with a linear increase in exposed internal surface area. The results are shown on the graph of FIG. 5.

When viewing the treated samples under a microscope, it was found that only the floury endosperm showed any appreciable degree of fluorescence due to the penetration of the ANS for short contact times— that is, shorter than about 30 minutes. The preferred time for applying the ANS is 2 minutes, as indicated above.

Having thus disclosed in detail a preferred embodiment of the invention, persons skilled in the art will be able to modify certain of the steps which have been disclosed and to substitute equivalent apparatus for that illustrated while continuing to practice the principle of the invention, and it is, therefore, intended that all such modifications and substitutions be covered as they are embraced within the spirit and scope of the appended claims.

We claim:

1. A method of measuring mechanical damage to grain comprising: applying a solution to a sample of the damaged grain for a predetermined time, said solution containing a material which selectively chemically bonds to interior protein of said grain, said interior protein having been exposed by said mechanical damage, and which does not bond to other portions of the grain to an appreciable extent, wherein the resulting products fluoresce when irradiated; grinding said sample grains to which said solution has been applied; exposing said ground sample to a source of radiation which induces said fluorescence; and measuring the induced fluorescence of the ground sample, which measurement defines the mechanical damage of said grain.

2. The method of claim 1 wherein said grain is kernel corn.

3. The method of claim 1 wherein said step of grinding comprises grinding said sample to substantially uniform particle size.

4. The method of claim 1 further comprising the step of spreading the ground sample over a predetermined area before exposing it to ultraviolet light.

5. The method of claim 1 further comprising the step of detecting induced fluorescence of said sample with a fiber optic conduit having a known conical acceptance window and spreading said sample out beneath said fiber optic conduit throughout the conical acceptance window thereof.

6. The method of claim 1 further comprising the step of washing said solution from said sample prior to grinding and drying said washed samples for convenience of handling.

7. The method of claim 1 wherein said solution contains ANS and said predetermined time is less than about 30 minutes.

8. The method of claim 1 wherein said application time is in the range of 1–2 minutes.

9. The method of claim 1 wherein said solution is a 0.05 percent solution of ANS.

10. A method of measuring the mechanical damage sustained by corn kernels comprising: selecting a sample of the damaged corn kernels; applying an aqueous solution of a reacting agent to said sample, said agent selectively bonding to the exposed fluory endosperm of said grain to form reaction products which fluoresce when irradiated; removing said solution after a predetermined time; washing excess solution from said sample; grinding said sample to substantially uniform particle size; spreading said ground sample over a known area; exposing the ground sample to a source of radiation which induces said fluorescence; and measuring the induced fluorescence of said sample, which measurement defines the mechanical damage sustained by the corn kernels.

* * * * *